US00PP26945P3

(12) United States Plant Patent

Lintott et al.

(10) Patent No.: US PP26,945 P3
(45) Date of Patent: Jul. 12, 2016

(54) *GAILLARDIA* PLANT NAMED 'SUNSET FLASH'

(50) Latin Name: *Gaillardia×grandiflora*
Varietal Denomination: Sunset Flash

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 79 days.

(21) Appl. No.: 14/544,054

(22) Filed: Nov. 19, 2014

(65) Prior Publication Data

US 2015/0150175 P1 May 28, 2015

Related U.S. Application Data

(60) Provisional application No. 61/963,168, filed on Nov. 25, 2013.

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A new cultivar of *Gaillardia* named 'Sunset Flash' that is distinguishable by a long blooming period, gray-green foliage, a compact, low-growing habit and single inflorescences composed of two rows of flat ray florets which are orange-red in color with yellow tips, is disclosed.

2 Drawing Sheets

Genus and species: *Gaillardia×grandiflora.*
Variety denomination: 'Sunset Flash'.

BACKGROUND

The present disclosure relates to a new and distinct cultivar of *Gaillardia* plant, also known as a blanket flower, a herbaceous perennial that is grown for use as an ornamental landscape and container plant. The new variety is known botanically as *Gaillardia×grandiflora* and will be referred to hereinafter by the variety name 'Sunset Flash'. *Gaillardia* is in the family Compositae, under which the commonly referred to "flower" is actually the inflorescence, and made up of smaller ray florets and disc florets. The ray florets themselves have the appearance of "petals".

'Sunset Flash' originated and was selected from a large population of hybrid seedlings from a *Gaillardia* breeding program which was started in 2006. The breeding program was conducted in a greenhouse nursery in West Sussex, United Kingdom. The aims of the breeding program were to produce novel combinations of flower colors and flower forms which are borne on well-branched plants with sturdy growth habits. The inventors carried out a controlled hybridization was carried out using combinations of selected named varieties and selected unnamed and unreleased seedlings retained from previous breeding cycles.

'Sunset Flash' was selected in 2009 for its vibrant orange-red colored flat ray florets with yellow tips which are produced from spring until fall and which do not fade with age. 'Sunset Flash' was also selected for its compact and naturally branching habit and high bud count.

The hybridization which led to the selection of 'Sunset Flash' was carried out during 2008 using a proprietary unreleased seedling raised by the inventors and known as 'G722-1' (unpatented) as the male parent and a proprietary unreleased seedling raised by the inventors and known as 'G716-1' (unpatented) as the female parent.

'Sunset Flash' was first asexually propagated in October 2009 in a greenhouse at the inventors nursery in West Sussex, United Kingdom using shoot cuttings taken from lateral branches. 'Sunset Flash' is stable and reproduces true to type in successive generations of asexual reproduction.

SUMMARY

The following traits have been repeatedly observed and represent the distinguishing characteristics of 'Sunset Flash'. 'Sunset Flash' has not been tested under all possible conditions and phenotypic differences may be observed with variations in environmental, climatic, and cultural conditions, without however, any variance in genotype.

1. 'Sunset Flash' exhibits a compact and naturally branching plant habit.
2. 'Sunset Flash' exhibits single inflorescences comprised of two rows or layers of flat ray florets which are orange-red in color with yellow tips.
3. The disc of 'Sunset Flash' is deep red in color, with a yellow center, when the inflorescence is fully expanded.
4. 'Sunset Flash' blooms continually from early spring until late fall.
5. 'Sunset Flash' exhibits neat, medium to small foliage.
6. After one year's growth in a 3 liter container, 'Sunset Flash' is 35 cm to 40 cm in height and 40 cm to 45 cm in width.
7. 'Sunset Flash' is hardy in USDA zone 5.

DESCRIPTION OF THE PHOTOGRAPHS

The accompanying color photographs illustrate the overall appearance of the new *Gaillardia* cultivar 'Sunset Flash' showing the colors as true as it is reasonably possible to obtain in colored reproductions of this type. Colors in the photographs may differ from the color values cited in the detailed botanical description, which more accurately describes the actual colors of the new variety 'Sunset Flash'.

DESCRIPTION OF THE NEW VARIETY

Figure 1:
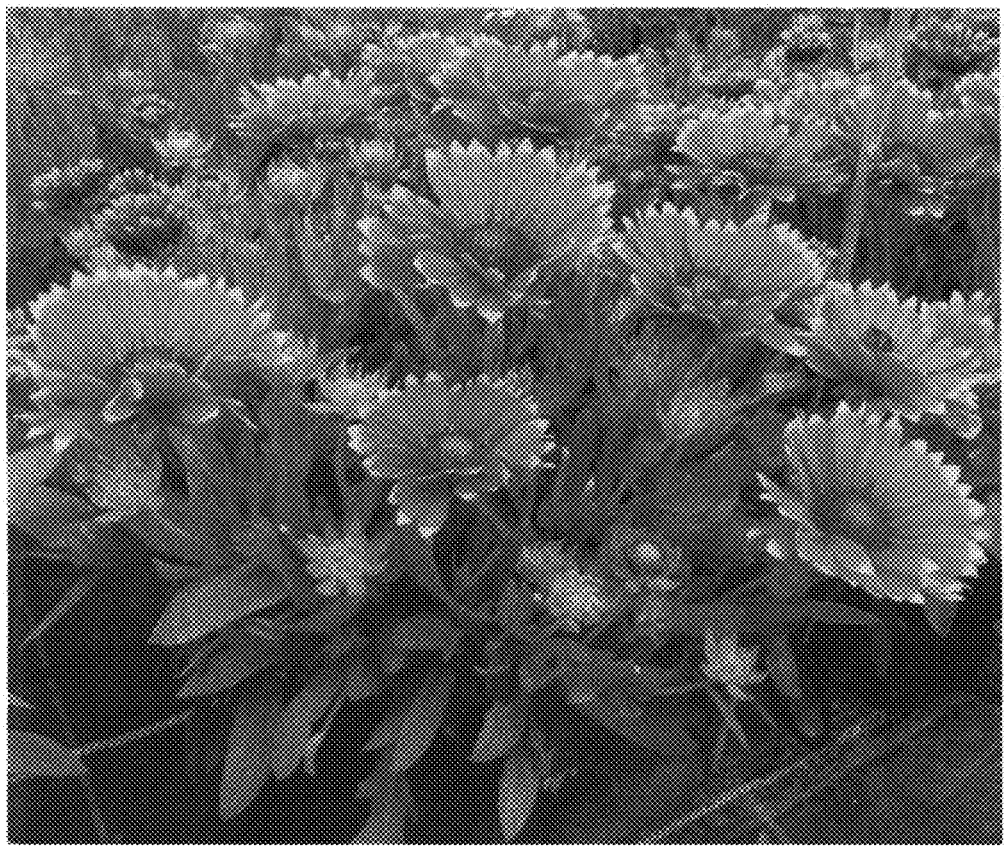
FIG. 1 depicts a whole plant of 'Sunset Flash' which has been grown in a frost-free greenhouse in West Sussex, United Kingdom. The illustrated plant is one year old and has been grown without any pinching or chemical growth regulator.
Figure 2:
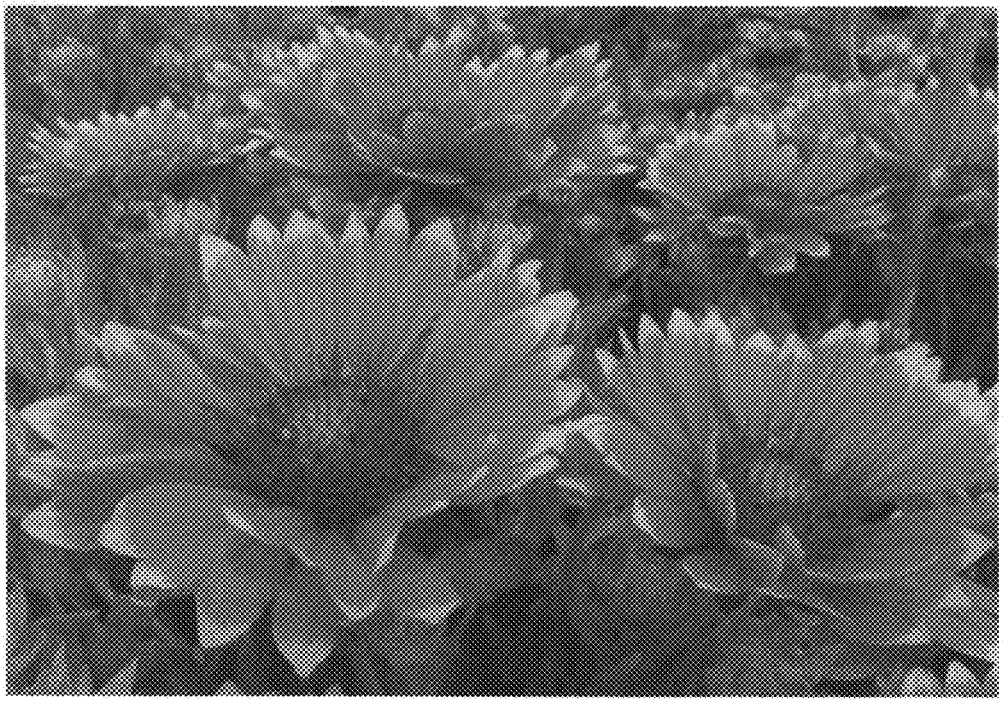
FIG. 2 depicts a close-up view of the fully expanded inflorescence of 'Sunset Flash'.

The following detailed descriptions set forth the distinctive characteristics of 'Sunset Flash'. Observations, measurements, values, and comparisons were collected in August, 2014 in Santa Barbara, Calif. from a one year old plant grown outdoors in in full sun in a 13 cm container with freely drained proprietary peat-based potting soil. Color determinations were made in accordance with the 2007 Royal Horticultural Society Colour Chart from London England, except where general color terms of ordinary dictionary significance are used.

Classification:

*Family.*—Compositae.

*Genus.*—*Gaillardia.*

*Species.*—×*grandiflora.*

*Common name.*—Blanket flower.

Parentage:

*Female parent.*—*Gaillardia* code number 'G716-1' (unpatented).

*Male parent.*—*Gaillardia* code number 'G722-1' (unpatented).

Plant:

*Propagation method.*—Typically by softwood cuttings although root cuttings have also been successful.

*Root system.*—Fine and fibrous.

*Vigor.*—Moderate vigor.

*Time to initiate roots.*—Approximately 14 to 20 days are needed to develop roots on initial cuttings.

*Temperatures to initiate rooting.*—The recommended air temperature is 20-21° Centigrade.

*Crop time.*—Approximately 10 weeks to 2 months are needed to produce a finished 15 cm container plant from a rooted cutting.

*Growth habit.*—Compact and naturally freely branching.

*Suggested container size.*—15 cm container.

*Use.*—Ornamental for use as a landscape plant or container plant.

*Type.*—Herbaceous perennial.

*Plant dimensions.*—After one year's growth in a 3 liter container: 35 cm to 40 cm in height and 40 cm to 45 cm in width. At maturity in the ground: 40 cm to 45 cm in height and 50 cm to 55 cm in width.

*Cultural requirements.*—Grow in full sun with moderate water, and well-draining soil such as loam.

*Hardiness.*—USDA Zone 5.

*Growing requirements.*—If grown outside in regions which experience winter freezing, 'Sunset Flash' may be started as a cutting during the spring or summer of the previous year, planted out prior to the onset of winter, and flowering will commence typically in May or June according to the region and season. When grown outside in frost-free regions, or in frost-protected greenhouses, 'Sunset Flash' will flower virtually all year round and may be started as a cutting (which should be non-flowering) at any time of year.

Stems:

*Branching habit.*—Basal branching.

*Stem color.*—138B.

*Stem dimensions.*—10 cm to 15 cm in length and 5 mm in width.

*Stem shape.*—Cylindrical, slightly fluted longitudinally.

*Stem surface.*—Markedly villous with dense coverage of very fine silvery hairs, approximately 3 mm to 4 mm in length.

*Internode length.*—Average internode length is 10 mm to 12 mm.

Foliage:

*Type.*—Evergreen.

*Leaf arrangement.*—Alternate.

*Margin.*—Entire.

*Leaf shape.*—Oblanceolate, except earlier (older) leaves exhibit one or two pairs of opposite lobes.

*Leaf dimensions* (*lobes absent*).—6.5 cm in length, 2.0 cm in width.

*Leaf dimensions* (*lobes present*).—7.5 cm in length, 2.5 cm in width at lobes.

*Leaf base.*—Truncate.

*Leaf apex.*—Acuminate.

*Leaf attachment.*—Sessile.

*Leaf color* (*both surfaces*).—138B.

*Leaf venation pattern.*—Parallel. Mid vein protrudes on both surfaces.

*Vein color* (*both surfaces*).—Lighter than 138B: between 138B and 138C.

*Leaf surface* (*both surfaces*).—Pubescent, very fine silvery hairs, lighter than 156D, approximately 3 mm in length.

*Fragrance.*—A slight sage-like scent when bruised.

Inflorescence:

*Inflorescence.*—Solitary.

*Aspect.*—Facing upward.

*Dimensions of inflorescence.*—80 mm in diameter and 15 mm in height.

*Inflorescence type.*—Radiate capitate with central disc.

*Disc diameter* (*inflorescence fully expanded*).—27 mm to 30 mm.

*Inflorescence number per plant.*—Approximately 25 to 30 inflorescences in bud and flower at one time.

*Blooming season.*—Spring, summer and fall.

*Lastingness of inflorescence.*—10 days, reducing to 7 days in full sun in mid-summer.

Peduncle:

*Peduncle dimensions.*—8 cm to 11 cm in length and 2.5 mm in diameter.

*Peduncle shape.*—Cylindrical.

*Peduncle surface.*—Surface is pubescent and exhibits longitudinal ridges.

*Peduncle color.*—138C.

*Peduncle strength.*—Stiff.

Flower buds:

*Bud shape.*—Rotate whorl.

*Bud dimensions* (*bud*).—13 mm in diameter and 9 mm in height.

*Bud color.*—138C.

*Bud surface.*—Villous.

Ray florets:

*Ray floret shape.*—Fan shaped with predominantly three but occasionally four fused petals appearing as lobes.

*Ray floret surface* (*outer surface*).—Pubescent.

*Ray floret surface* (*inner surface*).—Glabrous.

*Ray floret arrangement.*—Radiate.

*Number of ray florets per inflorescence.*—18 to 20 ray florets per inflorescence.

*Number of petals per ray floret.*—Three or four.

*Fused or unfused.*—Petals are basally fused.

*Petal margins of ray floret.*—Entire.

*Ray floret dimensions.*—28 mm to 30 mm in length including the corolla tube, 18 mm to 20 mm in width at the widest point.

*Corolla tube dimensions.*—3 mm in depth and 1 mm in diameter.

*Ray floret color* (*upper surface*).—42B except lobe tips (3 mm to 4 mm) 13A.

*Ray floret color* (*lower surface*).—180C except lobe tips (3 mm to 4 mm) 15C.

*Ray floret veins* (*both surfaces*).—Longitudinal, parallel, fine but prominent; color 53B.

*Self-cleaning or persistent.*—Self-cleaning.

Disc florets:

*Quantity of disc florets per inflorescence.*—Numerous, approximately 200 to 250.

*Disc floret dimensions* (*including pistil length*).—9 mm in length and 2.5 mm in width.

*Depth of disc floret corolla tube.*—6 mm.

*Surface of disc florets.*—Lanate.

*Color of disc florets* (*inflorescence newly opening, both surfaces*).—12A.

*Color of disc florets* (*inflorescence fully expanded, both surfaces*).—N34A.

*Phyllary.*—Dimensions: 5.50 cm in diameter and 3 cm in length. Color: 147B. Arrangement: Whorl.

*Involucral bracts.*—Number: An average of 25 per inflorescence Shape: Oblanceolate. Dimensions: 2 cm in length and 0.50 cm in width. Margin: Entire. Apex: Acute. Base: Truncate. Color (both surfaces): 138B. Surface texture (both surfaces): Pubescent.

*Fragrance of inflorescence.*—Sweet fragrance.

Reproductive organs:

*Stamens* (*present on disc florets only*).—Number: Three, adnate to inner surface of corolla tube. Dimensions: 0.20 mm in width and 5 mm in length. Color: 17A. Form: Plumose. Anther: Dimensions: 0.50 mm in length and 1 mm in width. Color: 187A. Shape: Narrow lanceolate. Pollen: Present. Quantity: Large amount. Color: 17B.

*Pistil* (*present on ray florets and disc florets*).—Number: One per floret. Pistil length: 12 mm in length. Style dimensions: 2 mm in length and 1 mm in width. Style color: 150D. Stigma: Dimensions: 8 mm in length and 1.75 mm in width. Form: Plumose. Color: 187A. Shape: Bifurcate. Ovary: Position: Inferior. Color: 150D. Shape: Globose. Dimensions: 1 mm in width and 2 mm in height.

Fruit/seed set:

*Number of seeds.*—Small to moderate amount (ranges from 50 to 100 seeds per inflorescence).

*Seed dimensions.*—5 mm to 6 mm in length (including hairs at apex) and 1 mm to 2 mm in diameter.

*Seed color.*—200A.

*Seed shape.*—Conical with rounded base and apex.

*Seed surface.*—Smooth except at the apex where many very fine silver hairs, up to 2 mm in length, are present in circular groups.

Disease and pest susceptibility: 'Sunset Flash' has not been observed to exhibit any resistance to any particular pest or disease. 'Sunset Flash' is susceptible to downy mildew and to thrips as may be typical of *Gaillardia.*

COMPARISON WITH PARENTAL LINES AND KNOWN VARIETY

'Sunset Flash' is distinguishable from the female parent, 'G716-1' as follows. The flowers of 'Sunset Flash' are composed of wider petals than the female parent. 'Sunset Flash' also exhibits a more compact growth habit than the female parent. Finally, 'Sunset Flash' has more colorfast flowers in both high light and high temperature conditions than the female parent.

'Sunset Flash' is distinguishable from the male parent, 'G722-1' as follows. Whereas the male parent exhibits carmine-pink florets with a cream tips, the florets of 'Sunset Flash' are orange-red in color with yellow tips. Additionally 'Sunset Flash' exhibits smaller foliage than the male parent.

The variety of *Gaillardia* which is considered to most closely resemble 'Sunset Flash' is the inventors' variety *Gaillardia* 'Sunset Snappy' (co-pending). Whereas the ray florets of 'Sunset Flash' are predominantly orange-red in color with yellow tips and arranged in two rows (layers), the ray florets of 'Sunset Snappy' are comprised of a single row of ray florets which are predominantly purple-pink in color, with cream-yellow tips.

'Sunset Flash' may also be compared with the variety, *Gaillardia* 'Oranges and Lemons' (U.S. Plant Pat. No. 17,092) which is similarly hardy. The flowers of 'Oranges and Lemons' are orange and yellow in color whereas the flowers of 'Sunset Flash' are orange-red in color with yellow tips. Additionally, the flowers of 'Sunset Flash' are larger and more abundant than those of 'Oranges and Lemons'. The plant habit of 'Sunset Flash' is more compact than that of 'Oranges and Lemons'.

We claim:

1. A new and distinct cultivar of *Gaillardia* plant named 'Sunset Flash' as described and illustrated herein.

* * * * *